(12) United States Patent
Li et al.

(10) Patent No.: US 10,845,284 B2
(45) Date of Patent: Nov. 24, 2020

(54) DROPLET-BASED MICROFLUIDIC RHEOMETER SYSTEM

(71) Applicant: REGENTS OF THE UNIVERSITY OF MICHIGAN, Ann Arbor, MI (US)

(72) Inventors: Yunzi Li, Ann Arbor, MI (US); Kevin R. Ward, Glen Allen, VA (US); Mark A. Burns, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 253 days.

(21) Appl. No.: 15/773,703

(22) PCT Filed: Nov. 4, 2016

(86) PCT No.: PCT/US2016/060445
§ 371 (c)(1),
(2) Date: May 4, 2018

(87) PCT Pub. No.: WO2017/079507
PCT Pub. Date: May 11, 2017

(65) Prior Publication Data
US 2018/0321123 A1    Nov. 8, 2018

Related U.S. Application Data

(60) Provisional application No. 62/251,832, filed on Nov. 6, 2015.

(51) Int. Cl.
*B01L 3/00*      (2006.01)
*G01N 11/04*    (2006.01)
(Continued)

(52) U.S. Cl.
CPC .......... *G01N 11/04* (2013.01); *G01N 33/4905* (2013.01); *G01N 2011/008* (2013.01);
(Continued)

(58) Field of Classification Search
CPC .......... B01L 3/00; G01N 11/04; G01N 35/00; G01N 33/48; G01N 33/4905;
(Continued)

(56) References Cited

U.S. PATENT DOCUMENTS 7,188,515 B2    3/2007  Burns et al.
8,056,398 B2   11/2011  Jakli et al.
(Continued)

FOREIGN PATENT DOCUMENTS

CN    201152848 Y    11/2008
CN    101819124 A     9/2010
(Continued)

OTHER PUBLICATIONS

International Application No. PCT/US2016/060445, International Search Report and Written Opinion, dated Feb. 22, 2017.
(Continued)

*Primary Examiner* — Brian J. Sines
(74) *Attorney, Agent, or Firm* — Marshall, Gerstein & Borun LLP (57) ABSTRACT

A droplet-based microfluidic rheometer system and method of use for real-time viscosity monitoring of blood coagulation is disclosed. Droplets of blood samples are generated in a microfluidic rheometer, and the size of the droplets is highly correlated to the sample viscosity. The size of the droplets can be determined optically using an inverted light microscope and a camera or using electrodes. The microfluidic rheometer systems provides viscosity measurements in less than a second and consumes less than 1µL blood or plasma over an hour period. The viscosity measurements may be displayed and transmitted to the Internet or cloud storage.

7 Claims, 5 Drawing Sheets

(51) Int. Cl.
*G01N 35/00* (2006.01)
*G01N 33/48* (2006.01)
*G01N 33/49* (2006.01)
*G01N 11/00* (2006.01)

(52) U.S. Cl.
CPC ............... *G01N 2011/0066* (2013.01); *G01N 2203/0089* (2013.01)

(58) Field of Classification Search
CPC ..... G01N 2011/0066; G01N 2011/008; G01N 2203/0089
See application file for complete search history.

(56) References Cited

U.S. PATENT DOCUMENTS

| | | | |
|---|---|---|---|
| 8,454,906 | B2 | 6/2013 | Mathies et al. |
| 8,961,903 | B2 | 2/2015 | Sadaba Champetier De Ribes et al. |
| 2006/0179923 | A1* | 8/2006 | Burns .................... G01N 11/06 73/54.07 |
| 2008/0014589 | A1 | 1/2008 | Link et al. |
| 2008/0311006 | A1 | 12/2008 | Bek et al. |
| 2011/0201009 | A1 | 8/2011 | Quake et al. |
| 2011/0268803 | A1* | 11/2011 | Prud'homme ....... A61K 9/1635 424/489 |
| 2013/0192349 | A1* | 8/2013 | Ramkumar ............ G01N 29/02 73/54.41 |
| 2014/0106382 | A1* | 4/2014 | Williamson .......... G01N 33/49 435/13 |
| 2015/0044696 | A1 | 2/2015 | Dothie et al. |

FOREIGN PATENT DOCUMENTS

| | | |
|---|---|---|
| CN | 102095670 A | 6/2011 |
| CN | 102147390 A | 8/2011 |
| CN | 102266734 A | 12/2011 |
| CN | 102486446 A | 6/2012 |
| CN | 103143405 A | 6/2013 |
| CN | 103988077 A | 8/2014 |
| CN | 103998928 A | 8/2014 |

OTHER PUBLICATIONS

Srivastava et al., Nanoliter viscometer for analyzing blood plasma and other liquid samples, Anal. Chem., 77(2):383-92 (Jan. 2005).
Srivastava et al., Electronic drop sensing in microfluidic devices: automated operation of a nanoliter viscometer, Lab Chip, 6(6):744-51 (Jun. 2006).
Livak-Dahl et al., Nanoliter droplet viscometer with additive-free operation, Lab Chip, 13:297-301 (2013).
DeLaMarre et al., Development of a Simple Droplet-Based Microfluidic Capillary Viscometer for Low-Viscosity Newtonian Fluids, Anal. Chem., 87: 4649-4657 (2015).

* cited by examiner

Container Filled With Oil, Oil Supply Line Plugged In, and Oil Fills Rheometer
204

Container Filled With Blood, Blood Supply Line Plugged In, and Droplets Formed
206

Size of Droplet Determined: Methods for Determination Include But Not Limited To Optical Method and Electrode-Based Method
208

Calculate Blood Viscosity Using Calibration Curve
210

DROPLET-BASED MICROFLUIDIC RHEOMETER SYSTEM

CROSS-REFERENCE TO RELATED APPLICATIONS

This application is the U.S. national phase of International Application No. PCT/US2016/060445, filed Nov. 4, 2016, which claims the benefit of the filing date of U.S. Provisional Application No. 62/251,832 filed Nov. 6, 2015, which is hereby incorporated by reference in its entirety.

FIELD OF THE DISCLOSURE

This application relates to a droplet-based microfluidic rheometer system for real-time viscosity monitoring of blood or plasma and of blood coagulation. Droplets of blood or plasma samples are generated in a microfluidic rheometer, and the size of the droplets is highly correlated to the sample viscosity. The microfluidic rheometer system provides viscosity measurements in less than a second and consumes less than 1 µl blood or plasma over an hour period.

BACKGROUND

Abnormalities in blood rheology and coagulation are a major cause of morbidity and mortality worldwide. In the field of trauma care, for example, uncontrollable bleeding caused by coagulopathy (i.e., coagulation abnormalities) is a major cause of preventable death. More than five million people die from trauma every year, accounting for 9% of global annual mortality, and at least one-fourth of trauma patients suffer from coagulopathy. Coagulopathy is also a major complication of sepsis and leads to rapid death. There are over one million cases of sepsis per year resulting in over 250,000 deaths. However, many of these deaths can be prevented through early diagnosis and treatment of coagulopathy. Although efforts have been made to develop tests that are able to monitor blood clotting and the subsequent fibrinolysis process, these tests suffer from low sensitivity and poor reproducibility across laboratories, and have failed to become standardized for acute care. The current routine coagulation assays, such as prothrombin time/international normalized ratio (PT/INR), provide no information on clot evolution and breakdown, thus limiting their ability to diagnose a broader range of coagulation abnormalities. For the most part, these traditional tests examine the accelular (or protein) component of coagulation. The viscoelasticity-based tests, such as throboelastography (TEG) or rotational throboelastometry (ROTEM) have poor reproducibility and accuracy, rendering them somewhat problematic for clinical purposes. They are also expensive and the footprint is large. Furthermore, neither type of test can monitor any changes in the blood before the clots form, such as innate viscosity and its dynamic changes. Neither Thromboelastography (TEG) nor Rotational Thrombelastometry (ROTEM) provide adequate test environments. Lastly, blood viscosity itself is known to change as a result of inflammation, thus making it a suitable candidate for monitoring in a host of cardiovascular and metabolic diseases associated with inflammation. These include but are not limited to sepsis, diabetes, infections, autoimmune diseases, hypertension, and many others.

SUMMARY

The current disclosure is directed to a fully automated microfluidic rheometer system for easy and quick measurement of blood or plasma viscosities in order to continuously monitor blood rheology and viscoelastic properties to include diagnosis of coagulation abnormalities in patients. Whole blood samples from the patient are collected and fed directly into a microfluidic rheometer. The blood or plasma from the sample is mixed with oil in the microfluidic rheometer and emulsifies to form droplets, and the size of the droplets is highly correlated to the sample viscosity. On-chip electrodes sense the differences in dielectric constants once a blood or plasma droplet is passed by. The signal is sent to a computer through a converter, and the size of the droplets is calculated. Once the oil type and feeding pressure are specified, such as by users, the viscosity of blood or plasma can be calculated based on the droplet size and displayed continuously in real-time. The rheometer generates multiple droplets per second depending on the feeding speed of the whole blood samples, thus allowing continuous viscosity measurement within a second. The rheometer is capable of operating on less than 1 µl blood over a one hour period. For a single viscosity measurement, a sample volume as low as 10 nl is enough for reliable viscosity measurements. Droplet lengths remain relatively constant with different sample volumes from 0.1 µl to 100 µl. The microfluidic rheometer can be calibrated and optimized to improve sensitivity and robustness by altering device geometry, channel size, feeding pressures of oil and blood, and oil viscosities.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE PREFERRED EMBODIMENTS

Figure 1:
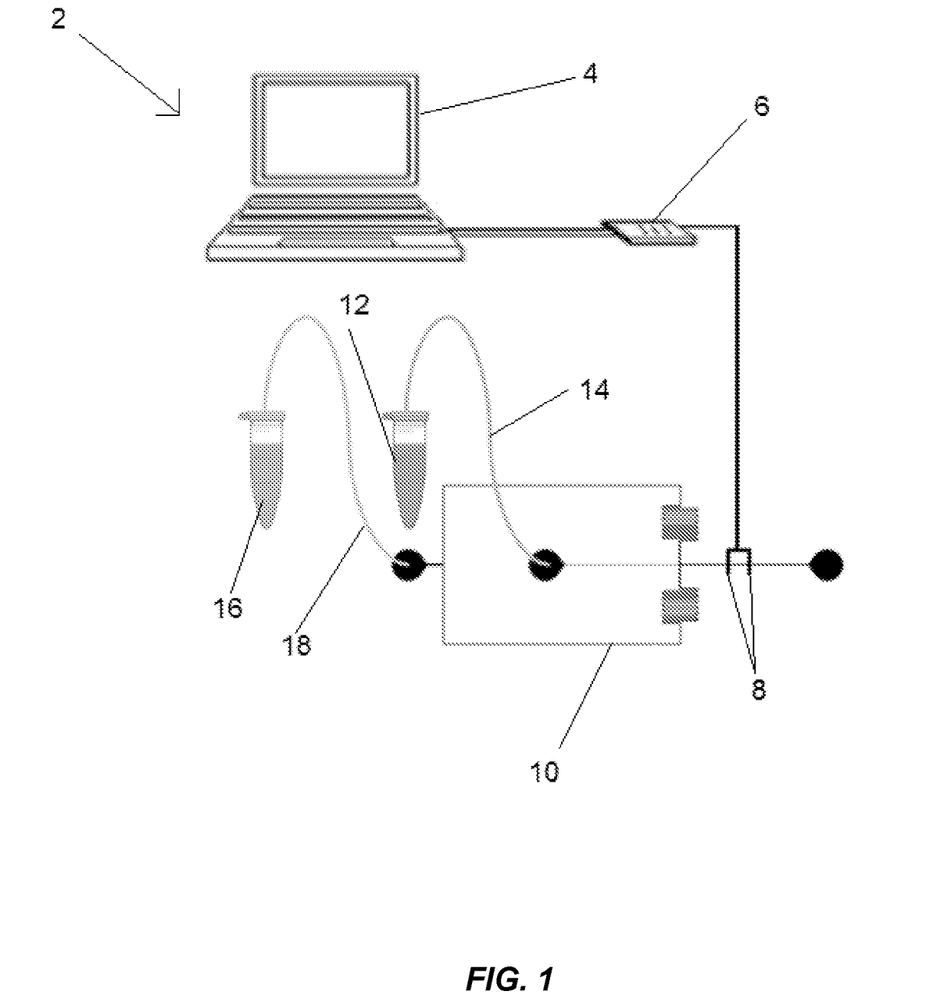
FIG. 1 illustrates schematically a microfluidic rheometer system for real-time viscosity monitoring of blood coagulation including a data collection/readout device, a capacitance-to-digital converter, electrodes for capacitance measurement, a microfluidic rheometer, whole patient blood samples, and oils for droplet generation.

Referring to the figures in detail, FIG. 1 illustrates an exemplary microfluidic rheometer system 2 including a data collection/readout device 4, such as a computer or a portable electronic device, connected to a capacitance-to-digital converter 6, which is connected to electrodes 8. The electrodes 8 measure capacitance generated by droplets in microfluidic rheometer 10, which are formed from whole blood samples provided to the microfluidic rheometer 10 from an aqueous container 12 through aqueous supply line 14 and oil provided to the microfluidic rheometer 10 from an oil container 16 through oil supply line 18. The blood or plasma from the samples and oil meet at the cross junction of the microfluidic rheometer 10 and emulsified to form the droplets. The electrodes 8 sense the differences in capacitance due to changes in dielectric constants once a droplet passes by. The signal is sent to the data collection/readout device 4 through the converter 6, and the size of the droplets is calculated. Once the oil type and feeding pressure are specified by users, the viscosity of blood or plasma can be calculated based on the droplet size and displayed continuously in real-time. The size of the droplets can be determined using an inverted light microscope, a camera, image capture software (not pictured), and image analysis software (not pictured). Alternately, the size of the droplets can be determined using the electrodes 8 and a software program can calculate the speed and size of the droplet.

The microfluidic rheometer 10 may be fabricated from glass wafers using traditional techniques. The glass rheometer 10 may include a first glass wafer that is fabricated to have patterned channels and a second glass wafer that has oil and aqueous inlet holes drilled into it. The two glass wafers may be coated to achieve hydrophobicity (discussed further below) and aligned and bonded. Inlet ports for the aqueous supply line 14 and oil supply line 18 may be created by gluing shoulder washers on top of the desired holes. The aqueous supply line 14 and oil supply line 18 may be PTFE tubes having an inner diameter of 0.022 inches. Pressures at the inlet ports may be measured using a digital pressure gauge.

The microfluidic rheometer system 2 is expected to find wide spread use in hospital and clinics including but not limited to outpatient anticoagulation clinics, general medicine and surgical clinics, cardiac surgery units, various intensive-care units, dialysis units, blood banks, trauma center and emergency rooms. The information provided will help health care providers make rapid decision regarding disease states, disease trajectories, transfusion and blood component utilization decisions, medication and dosage administration decisions, surgical decisions, and more. These health care providers will include Emergency Physicians, Hematologists, Intensivists, Surgeons, Blood Bankers, Diabetologists, Cardiologists, Anesthesiologists, Rheumatologists, Pharmacists, and many other medical and surgical subspecialists for both adult and pediatric patients. The information provided may help reduce the need for blood transfusion, provide personalized and precision medication management for patients at risk for either thrombosis or coagulopathy, and guide general inflammatory and autoimmune disease management.

Figure 2:
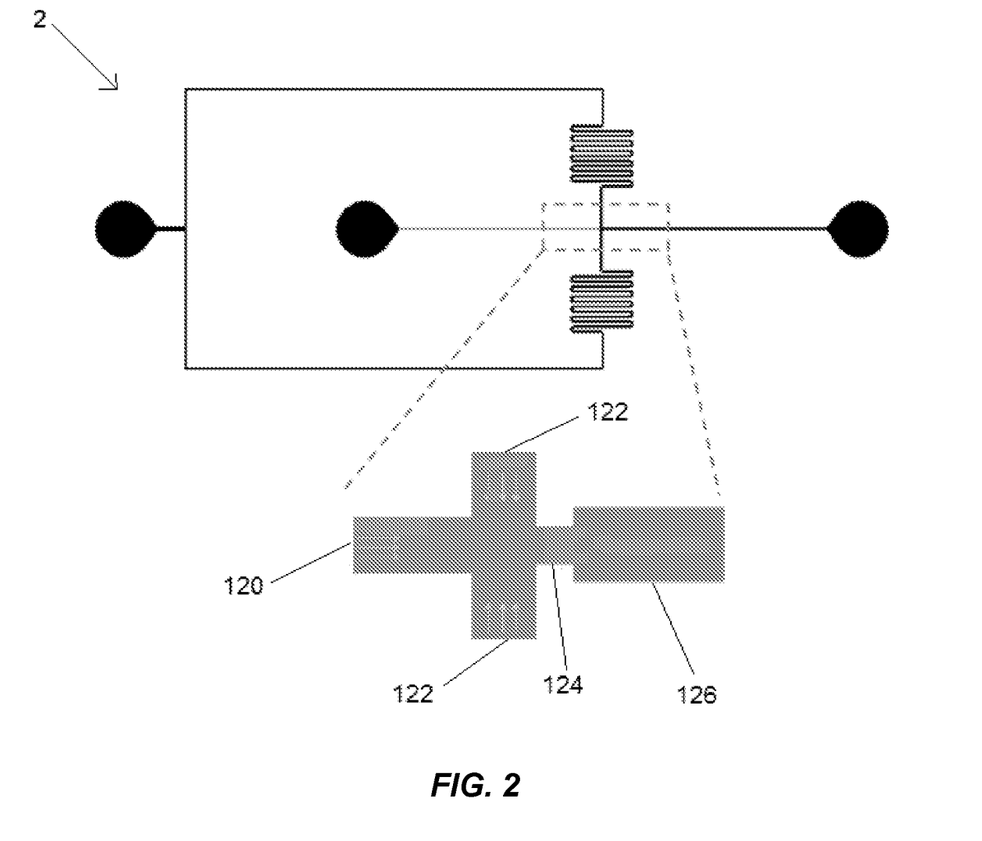
FIG. 2 illustrates the pathways within the microfluidic rheometer in which blood or plasma and fluid are mixed to form droplets.

FIG. 2 illustrates the various pathways within the microfluidic rheometer system 2 by which blood or plasma and fluid are mixed to form droplets. Blood or plasma or an aqueous solution enters through an aqueous inlet 120 that is between 10 and 1000 μm wide. Oil enters through an oil inlet 122 that is generally one to five times as wide as the aqueous inlet 120. The blood or plasma and oil mix into droplets while going through a constriction 124 and then entering a downstream channel 126. The constriction 124 is generally less than or equal in width to the blood inlet, and the downstream channel 126 is wider than the width of the constriction 124 but smaller than two times the size of the aqueous inlet 120. The depth of the downstream channel 126 is preferably on the order of 10 to 100 μm. In an embodiment, the aqueous inlet 120 is 60 μm wide, the oil inlet is 70 μm wide, the constriction is 40 μm long and 40 μm wide, and the downstream channel 126 is 80 μm wide. In some embodiments within the scope of the present disclosure, the aqueous supply line 14 and oil supply line 18 are pressurized, and the feeding pressure of the oil and blood or plasma is determined by the positive pressure settings of the aqueous supply line 14 and the oil supply line 18. In other embodiments within the scope of the present disclosure, a vacuum (not depicted) is attached to an outlet of the downstream channel 126. In such embodiments, the feeding pressures and shear stress of the blood or plasma and oil are created by a negative pressure at the outlet of the downstream channel 126 and can be varied as changing shear can be used as a provocative stimulus for coagulation and to gain further insights into viscosity and coagulation of blood or plasma.

The walls of the constriction 124 and the downstream channel 126 must have sufficient hydrophobicity in order to prevent the droplet size from changing over time. If the walls do not have sufficient hydrophobicity and residuals of the aqueous solutions adhere to the walls, the aqueous residuals may change the hydrophobicity of the walls and result in inconsistency in droplet size over time. For example, in some embodiments, polydimethylsiloxane (PDMS) may coat the walls of the constriction 124 and the downstream channel 126 to provide sufficient hydrophobicity. In other examples, 2 μm of parylene-C may coat the walls of the constriction 124 and the downstream channel 126 to provided sufficient hydrophobicity.

Figure 3:
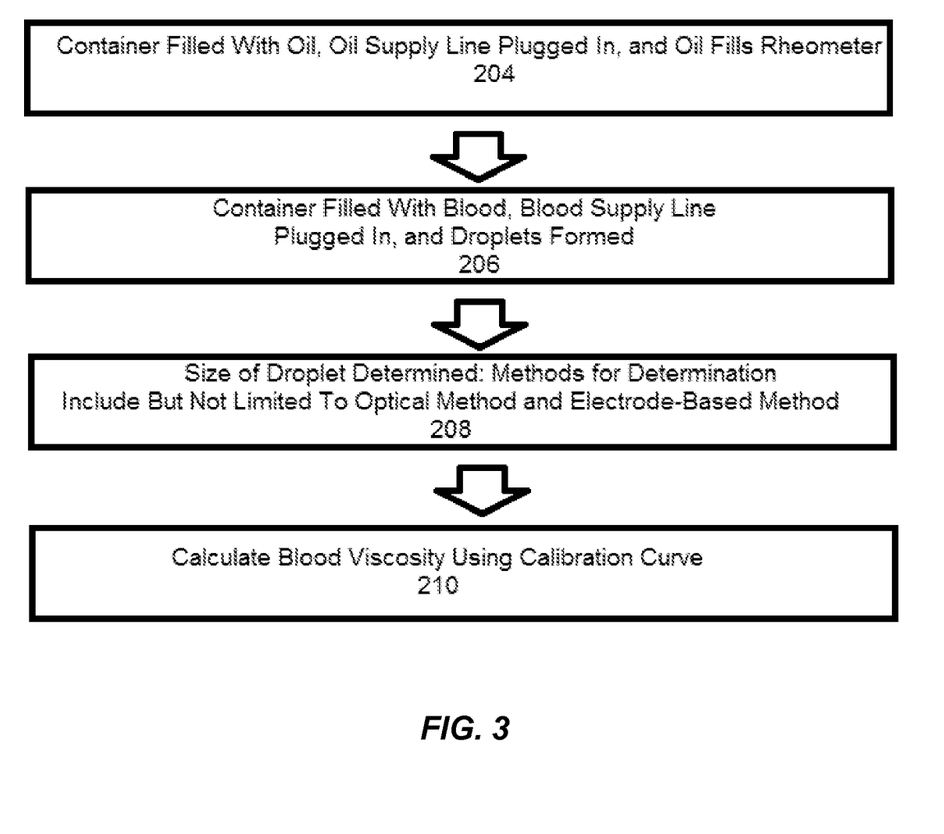
FIG. 3 is a flow chart illustrating a method of providing real-time viscosity data via use of a microfluidic rheometer system of the present disclosure.

FIG. 3 is a flow-chart illustrating a method of providing real-time viscosity data 202 via use of the microfluidic rheometer system 2. At box 204, the oil container 16 is filled with surfactant-added oil, and the oil supply line 18, which may be pressurized, is plugged into the microfluidic rheometer 10. Mineral oils may be used as the surfactant-added oil, and/or the selection of oil may be dictated by factors such as optimized wetting or interfacial tension effects. Sufficient time is allowed to pass for the oil supply line 18 and the oil inlet 122, constriction 124, and downstream channel 126 to fill with the oil. This generally takes less than one minute depending on channel dimensions. At box 206, the aqueous container 12 is filled with either fresh whole blood or recalcified citrated whole blood, and the aqueous supply line 14, which may be pressurized, is plugged into the microfluidic rheometer 10. Through additional filtration or microfluidic channels (not shown), plasma can be separate from whole blood if desired. As the blood or plasma from the blood mixes with the oil, droplets begin to be formed. Multiple droplets are generated per second by the microfluidic rheometer 10, thus allowing continuous viscosity measurement within a second. At box 208, the size of a droplet is determined. This may be done using an optical method or an electrode-based method. If the optical method is used, an inverted light microscope, a CCD camera, and image capture software such as OCapture is used to record the droplet generation at the downstream channel 126, and the size of the droplet is measured using an image analysis software such as ImageJ. In some embodiments, the inverted light microscope may have a 10× objective lens. If the electrode-based method is used, the electrodes 8 receive a peak signal (i.e., sense the differences in capacitance due to changes in dielectric constants) when a droplet passes through, the signal is sent to the data collection/readout device 4 through the capacitance-to-digital converter 6, and a LABVIEW™ or other development environment program is used to receive the signal and calculate the speed and size of the droplet. At box 210, a calibration curve is used to calculate blood or plasma viscosity based on droplet sizes. The calibration curve can be determined using glycerol/water solutions within the microfluidic rheometer 10. In some embodiments, the calibration curve shows a linear fitting law between log of droplet length versus log of viscosity. For instance, according to Hagen-Poiseuille law, $\Delta P \propto \eta Q$ (where $\Delta P$ is pressure difference, $\eta$ is solution viscosity, and Q is flow rate), is considered valid for an aqueous inlet channel of a fixed channel geometry. A user may provide oil type and feeding pressures for use in calculating the blood or plasma viscosity, and the range and sensitivity of the microfluidic rheometer can be optimized for different applications by changing device geometry, oil viscosity, and feeding speeds of the oil and blood or plasma. A working range of feeding pressures is governed by the ratio of aqueous feeding pressure to oil feeding pressure (AIP/OIP). Sensitivity of the microfluidic rheometer of the present disclosure increases with increasing AIP/OIP. In some embodiments, droplet generation occurs at AIP/OIPs from 0.25 to 0.80 and droplet distortion occurs at AIP/OIPs above 0.72.

Optionally, the calibration curve is input into a LABVIEW or similar development environment program so that the viscosity of the blood or plasma is automatically calculated and displayed. The information may further be transmitted to the Internet or cloud storage to enable a doctor to check in on a patient and to support big data analytic studies on blood clotting disorders. The total blood or plasma consumption of the rheometer for one-hour continuous measurement is typically less than 1 µl.

The platform may include multiple channels for multiplex testing of blood or plasma, allowing specific coagulation or inflammatory disorders to be more precisely defined. Using this strategy, channels may be pre-coated with various pro or anticoagulants or various pro and antiinflammatory agents which interact with either the cellular (red cell, white cell, platelet) component of blood or the acellular (protein) component. Alternatively, mixing chambers can be created which allow blood or plasma to be mixed with these agents prior to or after oil emulsification.

Figure 4:
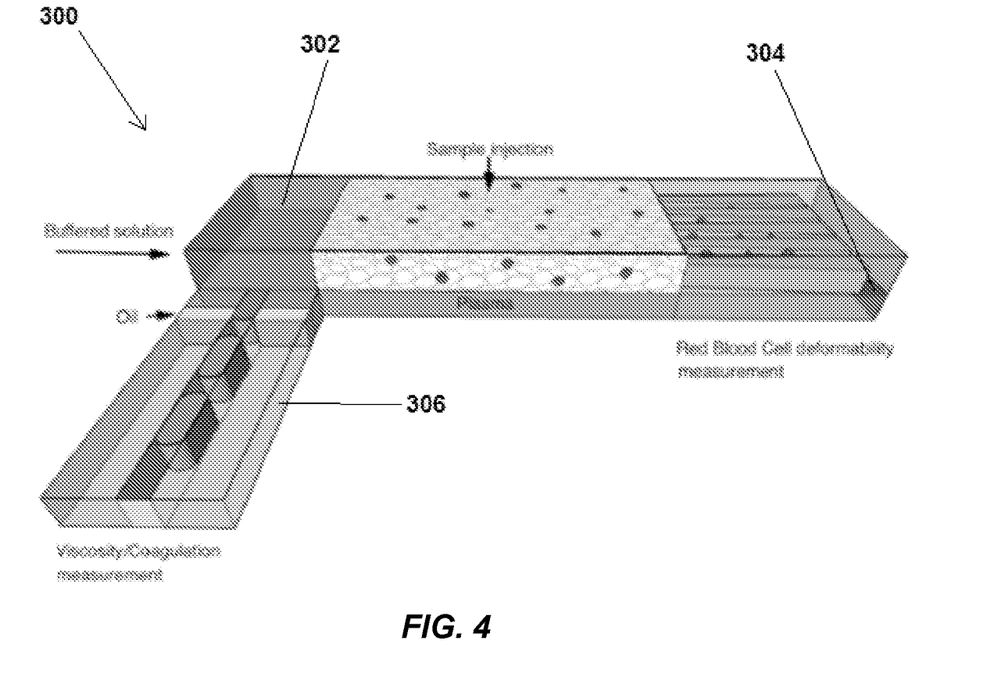
FIG. 4 illustrates a microfluidic rheometer system having a red blood cell deformability measurement system.

FIG. 4 depicts integration of a red blood cell deformability measurement system 302 into a microfluidic rheometer system 300. Red blood cell deformability is key in inflammation response processes and has been found to be associated with outcomes in cardiovascular disease, hypertension, sepsis, and other health related issues. Additionally, reduced deformability of red blood cells is a severe storage lesion in blood used for transfusion and has been associated with adverse outcomes. In the embodiment depicted in FIG. 4, the microfluidic rheometer system 2 depicted in FIG. 1 is adapted to measure plasma viscosity and is identified as a viscosity measurement system 306. A red blood cell deformability measurement system 302 is on top of the viscosity measurement system 306. The plasma sample passes through a separation membrane 304 before reaching the viscosity measurement system 306. In the red blood cell deformability system 302, the red blood cells flow through an obstructed path, and the stopping point of the red blood cells correlates to their deformability. In other embodiments, the viscosity measurement system 306 is adapted for whole blood samples, and half of the whole blood sample is delivered to the viscosity measurement system while the other half goes into the red blood cell deformability section.

Figure 5:
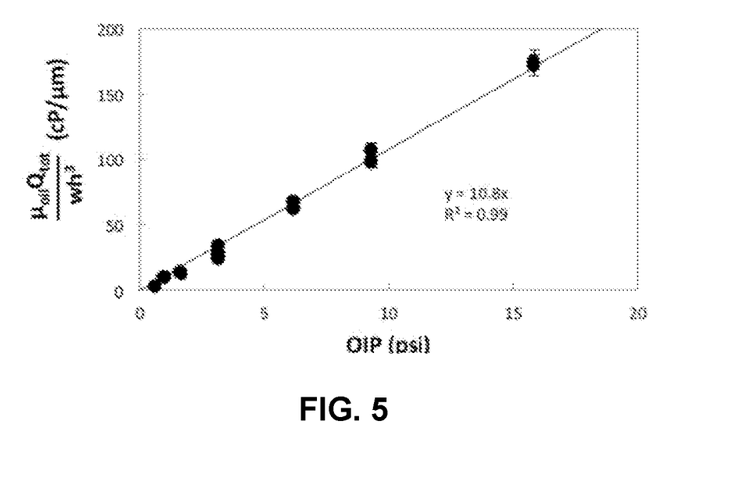
FIG. 5 is a graph illustrating the relationship between oil-inlet pressure (OIP), device geometry, and flow rate.

FIG. 5 is a graph illustrating the relationship between oil-inlet pressure (OIP), device geometry, and flow rate. Empirically, the relationship between OIP, device geometry, and flow rate, assuming w is the width of the channels, h is the channel depth, and $Q_{tot}$ is the total flow rate, was determined to be $OIP=(\mu_{oil}Q_{tot})/(10.8wh^3)$. The data supporting this empirical determination is discussed in Example 3 below.

EXAMPLES

Example 1

The relationship between the length of droplets and the ratio of aqueous-inlet to oil-inlet pressure (AIP/OIP) in the microfluidic rheometer system of the present disclosure was studied empirically. Glycerol and deionized water solutions with varying glycerol mass fraction were prepared for viscometer calibration. Light mineral oil with 5 wt % ABIL® EM 90 and heavy mineral oil with 5 wt % ABIL® EM 90 were prepared and used as the continuous phase for droplet generation. The cell culture medium contained M9 minimal medium with 36 g/l glucose (2 mM MgSO4, 0.1 mM CaCl2, 33.7 mM Na2HPO4, 22 mM KH2PO4, 8.55 mM NaCl, 9.35 mM NH4Cl, 3.6% glucose). Blood serum and blood plasma were Prepared from whole blood using standard protocols. Boger fluid (i.e., constant viscosity elastic fluid) was prepared by dissolving 8000 ppm polyethylene glycol in 78% glycerol solution. The viscosities of all aqueous solutions and oil/surfactant mixtures at 25° C. were measured on a cone-and-plate rheometer. The droplet-based microfluidic viscometer was used to measure the glycerol/water solutions. After connecting the oil reservoir to the chip, pressure was applied to the oil inlet to fill the channels with oil. Then, the aqueous sample was fed into the device and droplets were generated. Recordings and measurement were made after droplet generation become steady (typically in less than 1 minute). The image stacks were analyzed using ImageJ to measure the length and speed of the droplets, the spacing between two droplets and the generation time for one droplet.

The results showed that the length of the droplets ($L_d$) is highly correlated to the aqueous-phase viscosity ($\mu_{aq}$) at high ratios of aqueous-inlet to oil-inlet pressure (AIP/OIP), yielding a linear relationship between $\mu_{aq}$ and $1/(L_d-L_c)$ where $L_c$ is the minimal obtainable droplet length. Theoretical analysis verifies this linear relationship, and the resulting equations can be used to optimize the device geometry (i.e., channel widths, depths and lengths). The applicable range of viscosity measurements depends on the oil-phase viscosity ($\mu_{oil}$), and viscosities within the range of $0.01\mu_{oil}$ to $10\mu_{oil}$ can be measured reliably with less than 5% error.

Example 2

The lengths of droplets were measured when different volumes of aqueous solution ($\mu_{aq}$=72.5 cP) were pipetted into the device. All measurements were conducted at OIP=3.17 psi and AIP/OIP=0.65.

Figure 6:
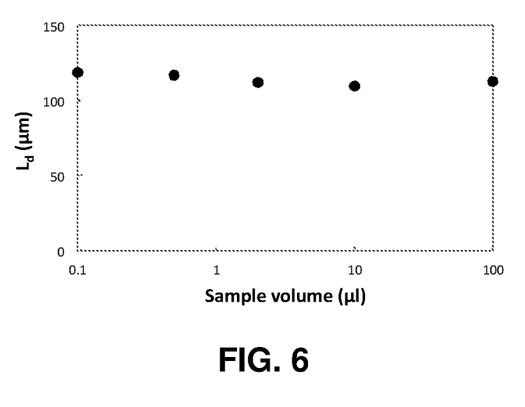
FIG. 6 is a plot of the measured length of droplets against the volumes of aqueous solution pipetted into the device, as described in Example 2.

As shown in FIG. 6, the droplet lengths remain relatively constant with different sample volumes from 0.1 µl to 100 µl.

Example 3

The relationship between oil-inlet pressure (OIP), device geometry, and flow rate was studied empirically to assist with design considerations of the microfluidic rheometer system of the present disclosure. Data was collected, shown below, on a total of eight rheometer systems with different geometries using two different oil viscosities and four different OIPs.

| Device # | h (μm) | w1 (μm) | w2 (μm) | w3 (μm) | L3 (μm) | oil viscosity (cP) |
|---|---|---|---|---|---|---|
| 1 | 5 | 15 | 25 | 25 | 8000 | 37 |
| 2 | 22.5 | 47.5 | 55 | 55 | 8000 | 37 |
| 3 | 22.5 | 47.5 | 55 | 55 | 8000 | 147 |
| 4 | 22.5 | 47.5 | 55 | 55 | 4000 | 37 |
| 5 | 41 | 74 | 82.5 | 82.5 | 8000 | 37 |
| 6 | 44 | 80 | 88 | 88 | 8000 | 147 |
| 7 | 60 | 94 | 111 | 111 | 8000 | 37 |
| 8 | 175 | 230 | 230 | 230 | 8000 | 37 |

Based on this data, a relationship between OIP, device geometry, and flow rate was determined. Assuming w is the width of the channels, which are comparable in width, h is the channel depth, and $Q_{tot}$ is the total flow rate, the relationship is:

$$OIP = (\mu_{oil} Q_{tot})/(10.8 w h^3)$$

This equation is applied in the table below.

| Device # | OIP (psi) | $\mu_{oil} Q_{tot}/(wh^3)$ (cP/μm) |
|---|---|---|
| 1 | 3.2 | 28.9 |
| 1 | 15.8 | 172.5 |
| 2 | 1.7 | 13.1 |
| 2 | 3.2 | 28.7 |
| 2 | 6.1 | 62.2 |
| 2 | 9.3 | 97.7 |
| 3 | 3.2 | 33.6 |
| 3 | 6.1 | 67.4 |
| 3 | 9.3 | 107.5 |
| 4 | 1.6 | 14.0 |
| 5 | 3.2 | 24.4 |
| 6 | 3.2 | 25.3 |
| 6 | 3.2 | 26.1 |
| 7 | 3.2 | 24.1 |
| 8 | 1.0 | 9.9 |

The empirical data closely matches the equation, as shown in FIG. 5.

Accordingly, $OIP = (\mu_{oil} Q_{tot})/(10.8 w h^3)$ can be considered a valid equation for a wide range of device geometry, oil viscosity, and operating pressures.

What is claimed is:

1. A method of using a microfluidic rheometer system comprising:
    filling an oil container with oil;
    plugging an oil supply line connected to the oil container into a microfluidic rheometer;
    allowing the microfluidic rheometer to fill with oil;
    filling an aqueous container with blood;
    plugging an aqueous supply line connected to the aqueous container into the microfluidic rheometer;
    mixing the oil and the blood or plasma from the blood to form droplets;
    determining the length of the droplets;
    calculating the viscosity of the blood or plasma based on the length of the droplets using a calibration curve relating the length of the droplets to the viscosity.

2. The method of using a microfluidic rheometer system of claim 1, and at least one of:
    determining the length of the droplets optically, and
    determining the length of the droplets using electrodes.

3. The method of using a microfluidic rheometer system of claim 2, and:
    determining the length of the droplets optically using an inverted light microscope and a camera to record droplet generation at a downstream channel of the microfluidic rheometer and measuring the size of the droplets using an image analysis software.

4. The method of using a microfluidic rheometer system of claim 2, and:
    determining the length of the droplets using electrodes includes the electrodes receiving a peak signal when a droplet passes the electrodes, the electrodes sending a signal to a data collection/readout device through a converter, and a development environment program of the data/collection readout device calculating the size of the droplets.

5. The method of using a microfluidic rheometer system of claim 1, and using the calibration curve includes
    calculating the calibration curve by putting water and glycerol solutions into the microfluidic rheometer.

6. The method of using a microfluidic rheometer system of claim 1, and at least one of:
    using 1 μl or less of blood or plasma to determine blood or plasma viscosity during an hour of continuous measurement,
    transmitting the viscosity of the blood or plasma to cloud storage or the Internet, and
    optimizing the microfluidic rheometer by changing device geometry, oil viscosity, feeding pressure, or shear stress of the oil or blood or plasma.

7. The method of using a microfluidic rheometer system of claim 2, and inputting at least one of oil type, oil supply line feeding pressure, shear stress, or aqueous supply line feeding pressure into a development environment program.

* * * * *